United States Patent [19]

Coates et al.

[11] Patent Number: 5,182,047

[45] Date of Patent: Jan. 26, 1993

[54] FLUORINATED BIPHENYLDIOLE DERIVATIVES

[75] Inventors: David Coates; Ian C. Sage, both of Dorset; Simon Greenfield, Poole, all of Great Britain

[73] Assignee: Merck Patent Gesellschaft mit beschraenkter Haftung, Darmstadt, Fed. Rep. of Germany

[21] Appl. No.: 399,541

[22] PCT Filed: May 20, 1989

[86] PCT No.: PCT/EP89/00558

§ 371 Date: Jul. 14, 1989

§ 102(e) Date: Jul. 14, 1989

[87] PCT Pub. No.: WO89/12039

PCT Pub. Date: Dec. 14, 1989

[30] Foreign Application Priority Data

Jun. 2, 1988 [GB] United Kingdom ............... 8813024

[51] Int. Cl.⁵ .................... C09K 19/12; C09K 19/30; C09K 19.34

[52] U.S. Cl. ..................... 252/299.66; 252/299.01; 252/299.63; 252/299.61

[58] Field of Search .............. 252/299.63, 299.66, 252/299.61, 299.01

[56] References Cited

U.S. PATENT DOCUMENTS

| 4,368,135 | 1/1983 | Osman et al. | 252/299.63 |
| 4,405,488 | 9/1983 | Sugimori et al. | 252/299.63 |
| 4,490,305 | 12/1984 | Eidenschink et al. | 252/299.63 X |
| 4,551,264 | 11/1985 | Eidenschunk et al. | 252/299.62 |
| 4,732,699 | 3/1988 | Higuchi et al. | 252/299.66 |
| 4,855,076 | 8/1989 | Goto et al. | 252/299.63 |
| 4,886,621 | 12/1989 | Sage et al. | 252/299.61 |
| 4,911,863 | 3/1990 | Sage et al. | 252/299.65 |

Primary Examiner—Robert L. Stoll
Assistant Examiner—C. Harris
Attorney, Agent, or Firm—Millen, White, Zelano and Branigan

[57] ABSTRACT

A chiral, tilted, smectic liquid crystal phase comprising a mixture of at least two compounds, wherein at least one compound is an achiral fluorinated biphenyldiole compound of formula I

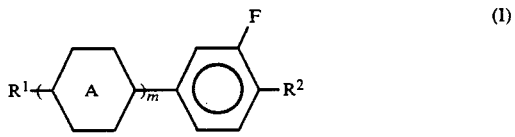

wherein
$R^1$ and $R^2$ are each independently alkoxy or alkanoyloxy with 1 to 15 C atoms,

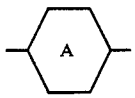

denotes a 4,4-phenylene group optionally substituted by up to four F atoms, and is 1.

5 Claims, No Drawings

FLUORINATED BIPHENYLDIOLE DERIVATIVES

The invention relates to fluorinated biphenyldiole derivatives of the formula I

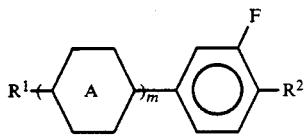

wherein
R$^1$ and R$^2$ a) are each independently alkoxy or alkanoyloxy with 1 to 15 C atoms, and wherein one CH2-group can also be replaced by —O—, —O—CO—, —CO—O— and/or —HC=CH— with the proviso that two O atoms are not directly linked, b) one of the residues R$^1$ and R$^2$ may also denote a group of the formula II

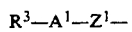

wherein

R$^3$ denotes an alkyl residue wherein one or two non-adjacent CH2-groups may also be replaced by —O—, —OCO—, —CO—O— and/or —HC=CH—, A$^1$ is a trans-1,4-cyclohexylene group, wherein one or two non-adjacent CH$_2$ groups may be replaced by —O— and/or —S—, a 1,4-bicyclooctylene group, or a 1,4-phenylene group, wherein one or two CH groups are replaced by N, and Z$^1$ is —CO—O— or —CH$_2$—O—, and/or c) one of the residues R$^1$ and R$^2$ may also denote a chiral group of the formula III

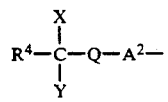

wherein

R$^4$ denotes an alkyl, alkoxy, alkanoyl-oxy or alkoxycarbonyl residue with 1 to 15 C atoms, X denotes H or CH$_3$, Y denotes CN, halogen, CH$_3$ or —OCH$_3$, Q denotes a single bond or an alkylene residue with 1 to 5 C atoms wherein one CH$_2$ group which is not linked to Z$^2$ can also be replaced by —O—, —O—CO—, —CO—O— or —CH=CH—, Z$^2$ is —CO—O, —O—CO—O— or —O—, with the proviso that the residues R$^4$, X and Y are different from each other,

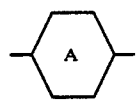

denotes a 1,4-phenylene group optionally substituted by up to four F atoms, and m is 1 or 2.

Chiral tilted smectic liquid crystal phases with ferroelectric properties can be prepared by adding a suitable chiral doping substance to base mixtures with one or more tilted smectic phases (L.A. Beresnev et al., Mol. Cryst. Liq. Cryst. 89, 327 (1982); H.R. Brand et al., J. Physique 44 (lett.), L-771 (1983)). Such phases can be used as dielectrics for rapidly switching displays based on the principle of SSFLC technology described by Clark and Lagerwall (N. A. Clark and S. T. Lagerwall, Appl. Phys. Lett. 36, 899 (1980); U.S. Pat. No. 4,367,924) on the basis of ferroelectric properties of the chiral tilted phase. In this phase, the longitudinally stretched molecules are arranged in layers, the molecules having a tilt angle relative to the normal of the layers. On advancing from layer to layer, the tilt direction changes by a small angle in respect of an axis vertical to the layers, so that a helix structure is formed. In displays based on the principle of SSFLC technology, the smectic layers are arranged vertical to the plates of the cell. The helical arrangement of the tilt direction of the molecules is suppressed by a very small distance between the plates (about 1-2 μm). The longitudinal axes of the molecules are thereby forced to align themselves in a plane parallel to the plates of the cell, which means that two distinct tilt orientations result. By applying a suitable alternating electrical field, a system can be switched back and forth between these two states in the liquid crystal phase which exhibits spontaneous polarization. This switching process is considerably more rapid than in conventional twisted cells (TN-LCDs) based on nematic liquid crystals.

The chiral compounds of the formula I which have three rings are partially covered by a broad formula of the European Patent Applications 01 53 826 and 02 43 209 wherein compounds of the formula

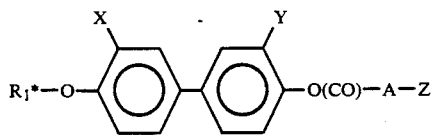

are claimed. But no compound according to this invention is disclosed there. Only compounds wherein X or Y denotes bromine or a cyano group are described. One skilled in the art, therefore, could neither infer how to synthesize these fluorinated compounds nor recognize that they show favourable mesophase ranges and an extraordinarily low viscosity.

Similar compounds e.g. are described in the European Patent Application 01 32 377 and the European Patent Application 02 36 215. But the compounds disclosed there are derivatives of 4,4'-disubstituted-2,2'-difluorobiphenyl.

A great disadvantage for many applications of the materials currently available with chiral tilted smectic phases (such as, for example, Sc*) is their low chemical, heat and light stability. Another adverse property of displays based on the chiral tilted smectic mixtures currently available is that high order smectic phases such as, for example, S$_I$, occur at low temperatures, so that the switch time properties of the displays are adversely influenced and/or the pitch and/or the tilt and/or the viscosity of the phases do not meet the requirements of display technology. Moreover, the temperature range of the ferroelectric phases is usually too small and is predominantly at temperatures which are too high.

It has now been found that the use of compounds of the formula I as components of chiral tilted smectic mixtures can substantially reduce the disadvantages mentioned. The compounds of the formula I are thus outstandingly suitable as components of chiral tilted smectic liquid crystal phases. In particular, chiral tilted smectic liquid crystal phases which are particularly chemically stable, have favourable viscosity values, in particular broad Sc* phase ranges, have an outstanding behaviour on supercooling down to temperatures below 0° C. without occurrence of high order smectic phases and have high spontaneous polarization values for such phases can be prepared with the aid of these compounds. P is the spontaneous polarization in $nC/cm^2$.

The compounds of the formula I have a wide range of applications. Depending on the choice of substituents, these compounds can be used as base materials from which liquid crystal smectic phases are predominantly composed; however, it is also possible for compounds of the formula I to be added to liquid crystal base materials from other classes of compounds, for example in order to vary the dielectric and/or optical anisotropy and/or the viscosity and/or the spontaneous polarization and/or the phase ranges and/or the tilt angle and/or the pitch of such a dielectric.

The invention thus relates to the compounds of the formula I, preferably to the compounds of the formula Ia

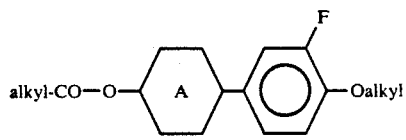

(Ia). The invention furthermore relates to chiral tilted smectic liquid crystal phases containing at least one compound of the formula I and liquid crystal display elements, in particular ferroelectric electrooptical display elements, containing such phases.

For simplicity, in the following text, Phe denotes an unsubstituted 1,4-phenylene group, PheF a 1,4-phenylene group substituted by up to F atoms, BCO a 1,4-bicyclo[2.2.2]octylene group, Az a heteroaromatic group selected from the group consisting of pyridine-2,5-diyl (Pyd), pyrimidine-2,5-diyl (Pyr), and pyridazine-2,5-diyl (Pyz) and Cyc denotes a trans-1,4-cyclohexylene group. Preferred compounds of the formula I are those of the part formulae Ia to If

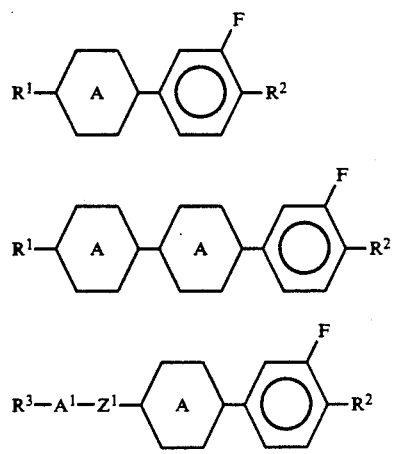

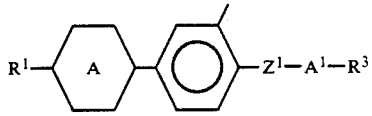

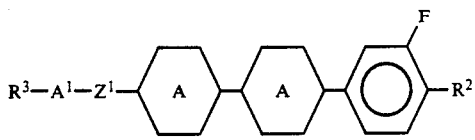

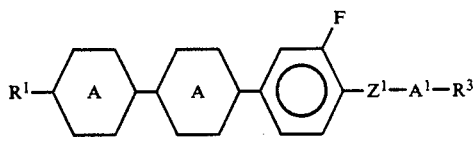

In the compounds of the part formulae Ia to If

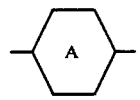

denotes a 1,4-phenylene group optionally substituted by up to four F atoms. Preferred are those compounds wherein A is an unsubstituted 1,4-phenylene group or a 2- (or 3-) fluoro-1,4-phenylene group.

In the part formulae Ic to If the group $A^1$ denotes preferably a 1,4-cyclohexylene group, a pyrimidine-2,5-diyl or a pyridine-2,5-diyl group.

In the part formulae Ic to If Z1 denotes a —CO—O— or —CH$_2$—O— group which is linked to the

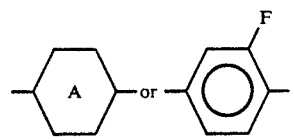

group by the oxygen.

Particularly preferred are the compounds of the part formulae I1 to I17, wherein PheF denotes a group of the formula

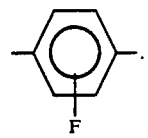

alkyl-O-Phe-PheF-OCO-alkyl I1
alkyl-O-PheF-PheF-OCO-alkyl I2
alkyl-O-PheF-PheF-O-alkyl I3
alkyl-O-Phe-PheF-O-alkyl I4
alkyl-CO-O-Phe-PheF-O-alkyl I5
alkyl-CO-O-Phe-Phe-PheF-O-alkyl I6
alkyl-CO-O-PheF-PheF-O-alkyl I7
alkyl-O-Phe-PheF-PheF-OCO-alkyl I8
alkyl-O-Phe-Phe-PheF-OCO-alkyl I9
alkyl-Cyc-CO-O-Phe-PheF-O-alkyl I10
alkyl-BCO-CO-O-Phe-PheF-O-alkyl I11
alkyl-Az-CO-O-Phe-PheF-O-alkyl I12
alkyl-O-Phe-PheF-O-CO-Cyc-alkyl I13
alkyl-O-Phe-PheF-O-CO-BCO-alkyl I14 alkyl-O-Phe-PheF-O-CO-Az-alkyl  I15
alkyl-O-Phe-PheF-O-CO-Az-O-alkyl  I16
alkyl-Az-CO-O-PheF-PheF-O-alkyl  I17

Particularly preferred compounds of the formulae I2, I3, I7 and I17 are those which exhibit a structure element of the formula 1

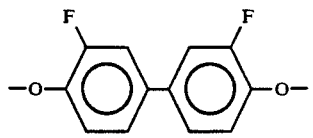

If $R^1$, $R^2$ and $R^3$ are each an alkyl residue and/or alkoxy residue, this radical can be straight-chain or branched. Preferably, it is straight-chain and has 5, 6, 7, 8, 9, 10, 11 or 12 C atoms and is accordingly preferably pentyl, hexyl, heptyl, octyl, nonyl, decyl, undecyl, dodecyl, pentyloxy, hexyloxy, heptyloxy, octyloxy, nonyloxy, decyloxy, undecyloxy or dodecyloxy, also tridecyl, tetradecyl, pentadecyl, tridecyloxy or tetradecyloxy.

Oxaalkyl is preferably straight-chain 2-, 3- or 4-oxapentyl, 2-, 3-, 4- or 5-oxahexyl, 2-, 3-, 4-, 5- or 6-oxaheptyl, 2-, 3-, 4-, 5-, 6-, or 7-oxaoctyl, 2-, 3-, 4-, 5-, 6-, 7- or 8- oxanonyl or 2-, 3-, 4-, 5-, 6-, 7-, 8- or 9-oxadecyl.

If $R^1$ and $R^2$ are each a group of the formula alkenyl-O, it can be straight-chain or branched. Preferably, it is straight-chain and has 4 to 10 C atoms. Alkenyl denotes accordingly, in particular, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl or dec-1-, -2-, -3-, -4-, -5-, -6-, -7-, -8- or -9-enyl.

Compounds of the formula I with branched terminal residues $R^1$ and $R^2$ can occasionally be of importance because of an improved solubility in the customary liquid crystal base materials, but in particular as chiral doping substances if they are optically active.

Branched groups of this type as a rule contain not more than one chain branching. Preferred branched residues $R^1$ and $R^2$ are isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

Formula I includes both the racemates of these compounds and the optical antipodes, as well as mixtures thereof.

Those of the compounds of the formulae I, Ia to If in which at least one of the residues contained therein has one of the preferred meanings mentioned are preferred.

Compounds of the formula I wherein the residue $R^1$ or $R^2$ denotes a chiral group of the formula III

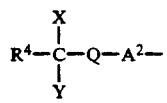   (III)

are particularly preferred.

Preferred chiral groups of the formula III are those of the part formulae IIIa to IIIg:

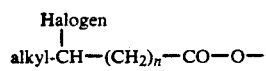   IIIa

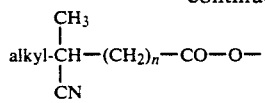   IIIb

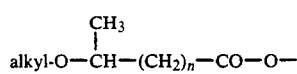   IIIc

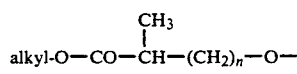   IIId

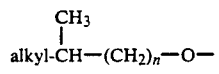   IIIe

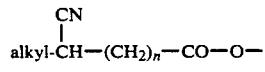   IIIf

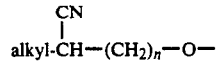   IIIg

In the groups of the formulae IIIa to IIIg n denotes 0 to 6, preferably n is 0. Halogen is preferably chlorine or fluorine.

Particularly preferred are those compounds of the formula I wherein the residue $R^1$ denotes a chiral group of the subformulae IIIa, IIIb, IIIc or IIIf or $R^2$ denotes a chiral group of the subformulae IIId, IIIe or IIIg.

The compounds of the formula I are prepared by methods which are known per se, such as are described in the literature (for example in the standard works, such as Houben-Weyl, Methoden der Organischen Chemie [Methods of Organic Chemistry], Georg-Thieme-Verlag, Stuttgart), and in particular under reaction conditions which are known and suitable for the reactions mentioned in more detail here can also be used in this connection.

If desired, the starting substances can also be formed in situ, such that they are not isolated from the reaction mixture but are immediately reacted further to give the compounds of the formula I.

Esters of the formula I can be obtained by esterification of corresponding carboxylic acids (or their reactive derivatives) with alcohols or phenols (or their reactive derivatives) preferably the corresponding carboxylic acid and the alcohol or phenol are reacted with water absorbing means as, for example, mol sieves or carbodiimides, particularly preferably with dicyclohexylcarbodiimide.

The corresponding carboxylic acids and alcohols or phenols are known or can be prepared by processes analogous to known processes.

Particularly suitable reactive derivatives of the carboxylic acids mentioned are the acid halides, above all the chlorides and bromides, and furthermore the anhydrides, for example also mixed anhydrides, preferably those of the corresponding carboxylic acids and trifluoroacetic acid formed in situ by mixing these carboxylic acids with trifluoroacetic anhydride, azides or esters, in particular alkyl esters with 1-4 C atoms in the alkyl group.

Possible reactive derivatives of the alcohols or phenols mentioned are, in particular, the corresponding metal alcoholates or phenolates, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as dimethylformamide or phosphoric acid hexamethyltriamide, hydrocarbons, such as benzene, toluene or xylene, halogenohydrocarbons, such as carbon tetrachloride, dichlormethane or tetrachloroethylene, and sulfoxides, such as dimethylsulfoxide or sulfolane. Water-immiscible solvents can simultaneously be advantageously used for azeotropic distillation of the water formed during the esterification. An excess of an organic base, for example pyridine, quinoline or triethylamine, can occasionally also be used as the solvent for the esterification. An additional, catalytic amount of 4-(N,N-dimethylamino)-pyridine can accelerate the esterification. The esterification can also be carried out in the absence of a solvent, for example by heating the components in the presence of sodium acetate. The reaction temperature is usually between $-50°$ and $+250°$, preferable between $-20°$ and $+80°$. At these temperatures, the esterification reactions have as a rule ended after 15 minutes to 48 hours.

In detail, the reaction conditions for the esterification depend largely on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is the reaction of an acid anhydride or, in particular, an acid chloride with an alcohol, preferably in a basic medium, bases which are of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises first converting the alcohol or phenol into the sodium alcoholate or phenolate or potassium alcoholate or phenolate, for example by treatment with ethanolic sodium hydroxide solution or potassium hydroxide solution, isolating this product and suspending it in acetone or diethyl ether, together with sodium bicarbonate or potassium carbonate, with stirring, and adding a solution of the acid chloride or anhydride in diethyl ether, acetone or diemthylformamide to this suspension, advantageously at temperatures between about $-25°$ and $+20°$.

Alkoxy compounds of the formula I ($R^1$ and/or $R^2$=O-alkyl) can be obtained by alkylation of the corresponding phenols, the phenol preferably first being converted into a phenolate for example into the alkali metal phenolate by treatment with NaOH, KOH, Na or $K_2CO_3$. This phenolate can then be reacted with the corresponding alkyl halide or sulfonate or dialkylsulfate, preferably in an inert solvent such as acetone, DMF or dimethylsulfoxide or an excess of aqueous or aqueous-alcoholic NaOH or KOH at temperatures between $0°$ and $100°$ C.

In the case that a chiral group of the part formulae IIId, IIIe or IIIf (n=0) is to be connected with a phenol, the corresponding optically active alcohol and the corresponding phenol are treated with triphenyl phosphine and diethyl azodicarboxylate as described by O. Mitsunobu, Synthesis 1981, 1.

Particularly preferred chiral tilted smectic liquid crystal phases according to the invention are those in which the achiral base mixture contains, in addition to compounds of the formula I, at least one other component with a negative or comparatively low positive dielectric anisotropy. This/these other component(s) of theachiral base mixture can make up 10 to 99%, preferably 50 to 95%, of the base mixture. Suitable further components with a comparatively low positive or negative dielectric anisotropy are compounds of the formulae IV to VIII.

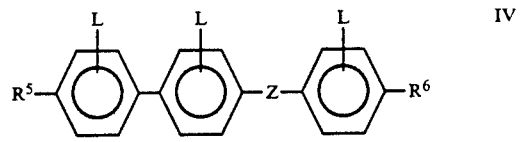

IV

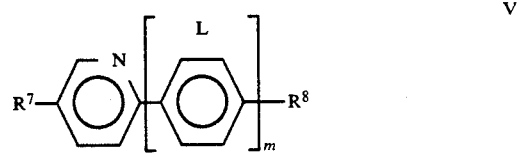

V

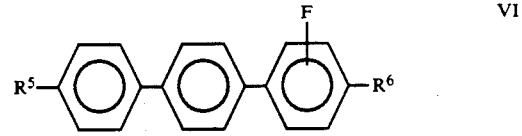

VI

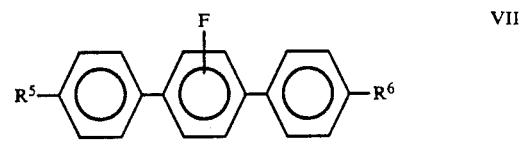

VII

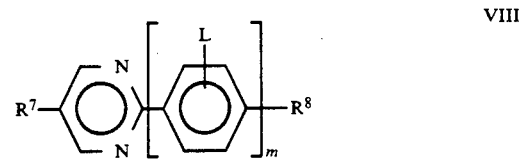

VIII wherein $R^5$, $R^6$ and $R^8$ are each alkyl or alkoxy with 5 to 15 C atoms, Z is —CO—O— or a single bond, L is hydrogen or fluorine, $R^7$ is alkyl with 5 to 15 C atoms and m is 1 or 2.

Preferred chiral dopants are those of formula IX

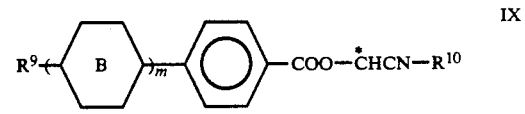

IX wherein $R^9$ is alkyl or alkoxy with 5 to 15 C atoms. $R^{10}$ is alkyl with 1 to 8 C atoms, m is 1 or 2, and - B - is 1,4-phenylene, pyridine-2,5-diyl, pyrimidine-2,5-diyl or trans-1,4-cyclohexylene.

The phases according to the invention are prepared in a manner which is customary, for example by mixing the components together, preferably at elevated temperatures.

The liquid crystal phases according to the invention can be modified by suitable additives so that they can be used in all the types of liquid crystal display elements hitherto disclosed.

The following examples are intended to illustrate the invention without limiting it. Percentages above and below are percentages by weight; all the temperatures are stated in degrees Celsius. The values given for spontaneous polarization are applicable to room temperature. The symbols are furthermore as follows: m.p.: melting point, C: crystalline solid state, S: smectic phase (the index characterizes the phase type), N: nematic state, Ch: cholesteric phase, I: isotropic phase. The figure between two symbols indicates the transition temperature in degrees Celsius.

EXAMPLE 1

Step 1

Preparation of 4-bromo-2-fluorooctyloxybenzene

A mixture of 4-bromo-2-fluorophenol (0.419 mol), 1-bromooctane (0.45 mol), potassium carbonate (110 g) and butanone (500 ml) is heated under reflux and stirred for 16 hrs. After cooling, the reaction mixture is filtered and the filtrate evaporated off, distillation under reduced pressure affords the required pure product.

Step 2

Preparation of 3-fluoro-4-octyloxyphenylboronic acid

The product from Step 1 (0.31 mol) is dissolved in dry tetrahydrofuran (250 ml); a small portion of this solution is added to a mixture of tetrahydrofuran and magnesium turnings (8.5 g) and the reaction initiated using iodine and gentle warming. Further bromo-compound solution is added at such a rate so as to maintain a gentle reflux. When all the bromo-compound has been added, the reaction mixture is refluxed for 1 h and then cooled, a further 120 ml of tetrahydrofuran is added. Under a nitrogen atmosphere, the Grignard reagent is slowly added to triisopropylborate (123 g) in tetrahydrofuran (10 ml) at −70 ° C. After the addition, the mixture is allowed to warm to 20 ° C. 10% hydrochloric acid solution (500 ml) is added and the organic layer separated, washed with brine and evaporated to give an oil which is subjected to a vacuum of 1 mm Hg at 20 ° C. for 1 h. The crude product is used in the next step.

Step 3

Preparation of 4-benzyloxy 4'-octyloxv-3'-fluoro-4-biphenyl

A mixture of the boronic acid from STEP 2 (0.098 mol), 4-benzyloxy-bromobenzene (0.081 mol), tetrakis triphenylphosphine palladium (0.5 g), 2M sodium carbonate (100 ml) methylated spirits (60 ml) and toluene (200 ml) is refluxed and stirred under nitrogen for 16 h. The cooled mixture is poured into water and extracted with dichloromethane, washed with water, dried and evaporated to give a pale yellow solid. After being chromatographed on 150 g of alumina, the purified product is crystallized from cyclohexane.

Step 4

Preparation of 4'-octyloxy-3'-fluoro-4-biphenol

The product from STEP 3 (0.57 mol) is dissolved in ethyl acetate (200 ml) and hydrogenated over Pd/C (1 g) until no further hydrogen is taken up. The mixture is then filtered, evaporated to dryness and crystallized from methanol.

Step 5

Preparation of 4'-octyloxy-3'-fluoro-4-biphenylyl nonanoate

The product from STEP 4 (0.0067 mol) is dissolved in cold dry dichloromethane (20 ml) and triethylamine (1 ml). Nonanoyl chloride (0.0073 mol) is added and the mixture stirred at 20 ° C. for 16 h. After the mixture has been washed with dilute hydrochloric acid and water, it is dried and evaproduct is chromatographed on silica and finally crystallized from methanol/ethyl acetate to give a white solid.

C 46.8 ° S 57.9 ° $S_c$ 87.5 ° I.

Analogously are obtained
4'-hexyloxy-3'-fluoro-4-biphenylyl-nonanoate
4'-heptyloxy-3'-fluoro-4-biphenylyl-nonanoate
4'-nonyloxy-3'-fluoro-4-biphenylyl-nonanoate
4'-decyloxy-3'-fluoro-4-biphenylyl-nonanoate
4'-octyloxy-3'-fluoro-4-biphenylyl-butyrate
4'-octyloxy-3'-fluoro-4-biphenylyl-pentanoate
4'-octyloxy-3'-fluoro-4-biphenylyl-hexanoate
4'-octyloxy-3'-fluoro-4-biphenylyl-heptanoate C 58.7° $S_c$ 86 0° I
4'-octyloxy-3'-fluoro-4-biphenylyl-decanoate, C 61.0° $S_c$ 89.1° I
4'-octyloxy-3'-fluoro-4-biphenylyl-(4-methylhexanoate), 46.9° $S_c$ 62.5° I

EXAMPLE 2

Preparation of 4'-octyloxy-3'-fluoro-4-biphenylyl (4-octylbicyclo[2.2.2octylcarboxylate)

4-Octylbicyclo[2.2.2]octylcarboxylchloride (0.0055 mol) is added to a mixture of 4'-octyloxy-3'-fluoro-4-biphenol (0.005 mol/product from Example 1, STEP 4), dry dichloromethane (20 ml) and triethylamine (1 ml). The mixture is stirred for at 20 ° C. for 24 h. After the mixture has been washed with dilute hydrochloric acid and water, it is dried and evaporated to give a colourless solid. The crude product is chromatographed in silica and finally crystallized from methanol/ethyl acetate to give a white solid, C<20° S 49.9° $S_B$ 125 ° $S_A$ 187.5° I.

Analogously are obtained:
4'-octyloxy-3'-fluoro-4-biphenylyl (4-ethylbicyclo[2.2.2]octylcarboxylate)
4'-octyloxy-3'-fluoro-4-biphenylyl (4-propylbicyclo2.2.2]octylcarboxylate)
4'-octyloxy-3'-fluoro-4-biphenylyl (4-butylbicyclo2.2.2]-octylcarboxylate)
4'-octyloxy-3'-fluoro-4-biphenylyl (4-pentylbicyclo2.2.2-octylcarboxylate)
4'-octyloxy-3'-fluoro-4-biphenylyl (4-hexylbicyclo[2.2.2]octylcarboxylate)
4'-octyloxy-3'-fluoro-4-biphenylyl (4-heptylbicyclo[2.2.2]octylcarboxylate)
4'-octyloxy-3'-fluoro-4-biphenylyl (4-nonylbicyclo[2.2.2]octylcarboxylate)
4'-octyloxy-3'-fluoro-4-biphenylyl (4-decylbicyclo[2.2.2]octylcarboxylate)
4'-octyloxy-3'-fluoro-4-biphenylyl (trans-4-ethylcyclohexylcarboxylate)
4'-octyloxy-3'-fluoro-4-biphenylyl (trans-4-propylcyclohexylcarboxylate)
4'-octyloxy-3'-fluoro-4-biphenylyl (trans-4-butylcyclohexylcarboxylate)
4'-octyloxy-3'-fluoro-4-biphenylyl (trans-4-pentylcyclohexylcarboxylate)

4'-octyloxy-3'-fluoro-4-biphenylyl (trans-4-hexylcyclohexylcarboxylate), C 39.9° $S_c$ 105.7° $S_A$ 173.1° I
4'-octyloxy-3'-fluoro-4-biphenylyl (trans-4-heptylcyclohexylcarboxylate), C 43.3° $S_c$ 111.2° $S_A$ 174.6° I
4'-octyloxy-3'-fluoro-4-biphenylyl (trans-4-octylcyclohexylcarboxylate), C 27.8° $S_c$ 112.3° $S_A$ 171.1° I
4'-octyloxy-3'-fluoro-4-biphenylyl (trans-4-nonylcyclohexylcarboxylate)
4'-octyloxy-3'-fluoro-4-biphenylyl (5-ethylpyrimidine-2-yl-carboxylate)
4'-octyloxy-3'-fluoro-4-biphenylyl (5-propylpyrimidine-2-yl-carboxylate)
4'-octyloxy-3'-fluoro-4-biphenylyl (5-butylpyrimidine-2-yl-carboxylate)
4'-octyloxy-3'-fluoro-4-biphenylyl (5-pentylpyrimidine-2-yl-carboxylate)
4'-octyloxy-3'-fluoro-4-biphenylyl (5-hexylpyrimidine-2-yl-carboxylate)
4'-octyloxy-3'-fluoro-4-biphenylyl (5-heptylpyrimidine-2-ylcarboxylate)
4'-octyloxy-3'-fluoro-4-biphenylyl (5-octylpyrimidine-2-ylcarboxylate)

EXAMPLE 3

Preparation of optically active
4'-octyloxy-3'-fluoro-4-biphenylyl
(2-chloro-3-methylbutyrate)

A mixture of dicyclohexylcarbodiimide (0.005 mol) and dichloromethane (20 ml) is added to a mixture of optically active 2-chloro-3-methylbutyric acid (obtained from 1-valine/0.005 mol), 4'-octyloxy-3'-fluoro-4-biphenol (Example 1, STEP 4/0.005 mol), 4-dimethylaminopyridine (0.005 mmol) and dichloromethane (25 ml). After stirring reaction the mixture is stirred at 20° C. for 12 h, it is filtered, the filtrate is evaporated off. The crude product is chromatographed on silica finally crystallized from methanol/ethyl acetate to give the required product as a colourless solid, C 42° I.

Analogously the following optically compounds are obtained:
4'-ethyloxy-3'-fluoro-4-biphenylyl (2-chloro-3-methylbutyrate)
4'-propyloxy-3'-fluoro-4-biphenylyl (2-chloro-3-methylbutyrate)
4'-butyloxy-3'-fluoro-4-biphenylyl (2-chlor 1butyrate)
4'-pentyloxy-3'-fluoro-4-biphenylyl (2-chloro-3-methylbutyrate)
4'-hexyloxy-3'-fluoro-4-biphenylyl (2-chloro-3-methylbutyrate)
4'-heptyloxy-3'-fluoro-4-biphenylyl (2-chloro-3-methylbutyrate)
4'-nonyloxy-3'-fluoro-4-biphenylyl (2-chloro-3-methylbutyrate)
4'-decyloxy-3'-fluoro-4-biphenylyl (2-chloro-3-methylbutyrate)
4'-octyloxy-3'-fluoro-4-biphenylyl (2-chloro-4-methylpentanoate)
4'-octyloxy-3'-fluoro-4-biphenylyl (2-fluoro-3-methylpentanoate)

EXAMPLE 4

Preparation of optically active ethyl
(2-4'-octyloxy-3'-fluoro-4-biphenyloxy)-propionate)

A mixture of diethyl azodicarboxylate (0.17 mol) and 100 ml tetrahydrofuran is added to a mixture of 4'-octyloxy-3'-fluoro-4-biphenole (0.15 mol), L(-)-ethyllactate (0.17 mol) and triphenylphosphine (0.15 mol). The mixture is stirred at 50° C for 1 h and at 20° C for 16 h. The solvens is evaporated off, the residue is dissolved in hot toluene and cooled to 20° C. The mixture is filtered, evaporated to dryness and chromatographed on silica to give a colourless solid.

The following optically active compounds are obtained analogously.
ethyl (2-(4'-ethyloxy-3'-fluoro-4-biphenyloxy)-propionate)
ethyl (2-(4'-propyloxy-3'-fluoro-4-biphenyloxy)-propionate)
ethyl (2-(4'-butyloxy-3'-fluoro-4-biphenyloxy)-propionate)
ethyl (2-(4'-pentyloxy-3'-fluoro-4-biphenyloxy)-propionate)
ethyl (2-(4'-hexyloxy-3'-fluoro-4-biphenyloxy)-propionate)
ethyl (2-(4'-heptyloxy-3'-fluoro-4-biphenyloxy)-propionate)
benzyl (2-(4'-ethyloxy-3'-.fluoro-4-biphenyloxy)-propionate)
benzyl (2-(4'-propyloxy-3'-fluoro-4-biphenyloxy)-propionate)
benzyl (2-(4'-butyloxy-3'-fluoro-4-biphenyloxy)-propionate)
benzyl (2-(4'-pentyloxy-3'-fluoro-4-biphenyloxy)-propionate)
benzyl (2-(4'-hexyloxy-3'-fluoro-4-biphenyloxy)-propionate)
benzyl (2-(4'-heptyloxy-3'-fluoro-4-biphenyloxy)-propionate)
benzyl (2-(4'-octyloxy-3'-fluoro-4-biphenyloxy)-propionate)

EXAMPLE 5

Preparation of optically active
2-4'-octyloxy-3'-fluoro4-biphenyloxy)-propionitrile Oxalylchloride (0.02 mol) is added to a mixture of optically active 2-(4'-octyloxy-3'-fluoro-4-biphenyloxy)-propionic acid (obtained from the corresponding benzylester (product of Example 4) by hydrogenolytic cleavage, 0.01 mol), benzene (50 ml) and catalytic amounts of dimethylformamide. After evaporating the mixture is dissolved in glyme (30 ml). A solution of ammonium hydroxide (25 ml, 30%) is added to the mixture. This mixture is stirred at 20° C. for 2 h. After diluting with water the mixture is filtered and the residue is dried in vacuo. This residue is dissolved in dimethylformamide (40 ml). After adding thionylchloride (0.08 mol) the mixture is stirred at 20° C. for 2 h. 10% hydrochloride acid solution (60 ml) and ether (100 ml) are added and the organic layer separated, washed with brine and evaporated. After being chromatographed on silica the purified product gives a white solid.

Analogously the following optically active compounds are obtained:
2-(4'-ethyloxy-3'-fluoro-4-biphenyloxy)-propionitrile
2-(4'-propyloxy-3'-fluoro-4-biphenyloxy)-propionitrile
2-(4'-butyloxy-3'-fluoro-4-biphenyloxy)-propionitrile
2-(4'-pentyloxy-3'-fluoro-4-biphenyloxy)-propionitrile
2-(4'-hexyloxy-3'-fluoro-4-biphenyloxy)-propionitrile
2-(4'-heptyloxy-3'-fluoro-4-biphenyloxy)-propionitrile

EXAMPLE 6

Preparation of 4,4'-dioctyloxy-3,3'-difluorobiphenyl

A mixture of 4'-octyloxy-3,3'-difluorobiphenol (0.1 mol, obtained by coupling 3-fluoro-4-octyloxyphenyl boronic acid with 4-benzyloxy-3-fluoro-brombenzene followed by hydrogenolytic cleavage of the benzylic ether), 1-bromooctane (0.12 mol), potassium carbonate (30 g) and butanone (125 ml) is heated under reflux and stirred for 20 hrs. After cooling the reaction mixture is filtered and the filtrate evaporated off, distillation under reduced pressure affords the required product, m.p. 84°.

Analogously are obtained:
4,4'-dimethoxy-3,3'-difluorobiphenyle m.p. 150°
4,4'-diethoxy-3,3'-difluorobiphenyle
4,4'-dipropyloxy-3,3'-difluorobiphenyle
4,4'-dibutyloxy-3,3'-difluorobiphenyle
4,4'-dipentyloxy-3,3'-difluorobiphenyle
4,4'-dihexyloxy-3,3'-difluorobiphenyle
4,4'-diheptyloxy-3,3'-difluorobiphenyle
4'-octyloxy-3,3'-difluoro-4-methyloxybiphenyle
4'-octyloxy-3,3'-difluoro-4-ethyloxybiphenyle
4'-octyloxy-3,3'-difluoro-4-propyloxybiphenyle
4'-octyloxy-3,3'-difluoro-4-butyloxybiphenyle
4'-octyloxy-3,3'-difluoro-4-hexyloxybiphenyle
4'-octyloxy-3,3'-difluoro-4-heptyloxybiphenyle

EXAMPLE 7

Preparation of 4'-octyloxy-3,3'-difluoro-4-biphenyl-yl nonanoate

4'-octyloxy-3,3'-difluorobiphenol (0.01 mol) is dissolved in dry dichloromethane (25 ml) and triethylamine (1 ml). Nonanoyl chloride (0.012 mol) is added and the mixture is stirred at 20 °C for 16 hrs. After washing with dilute hydrochloric acid and water the mixture is dried and evaporated. The crude product is chromatographed on silica and finally crystallized to give a colourless solid.

Analogously are obtained
4'-octyloxy-3,3'-difluoro-4-biphenylyl acetate, m.p. 67°
4'-octyloxy-3,3'-difluoro-4-biphenylyl propionate
4'-octyloxy-3,3'-difluoro-4-biphenylyl butyrate
4'-octyloxy-3,3'-difluoro-4-biphenylyl pentanoate
4'-octyloxy-3,3'-difluoro-4-biphenylyl hexanoate
4'-octyloxy-3,3'-difluoro-4-biphenylyl heptanoate
4'-octyloxy-3,3'-difluoro-4-biphenylyl octanoate
4'-octyloxy-3,3'-difluoro-4-biphenylyl (2-chloro-3-methylbutyrate)
4'-octyloxy-3,3'-difluoro-4-biphenylyl (2-chloro-3-methylpentanoate)
4'-octyloxy-3,3'-difluoro-4-biphenylyl (2-chloro-3-4-methylpentanoate)

EXAMPLE 8

A liquid crystal mixture consisting of
49% of 2-fluoro-4-heptylphenyl-3'-fluoro-4'heptyloxy biphenyl-4-ylcarboxylate and
51% of 3'-fluoro-4'-octyloxy-4-biphenylylnonanoate
exhibits S 30° S$_c$ 93.8 ° N 99.6 ° I.

EXAMPLE 9

A liquid crystal mixture consisting of
30.3% of 4-pentyl-2-fluorophenyl 4'-octyloxybiphenyl-4-ylcarboxylate
30.3% of 4-pentyl-2-fluorophenyl 4'-octylbiphenyl-4-ylcarboxylate
30.3% of 4-heptyl-2-fluorophenyl 4'-heptyloxybiphenyl-4-ylcarboxylate
14.0% of 4-(2-methylbutyl)-2-fluorophenyl 4'-octyloxybi-phenyl-4-ylcarboxylate
50% of optically active S-1-cyanoethyl 4-nonyloxybiphenyl-4-ylcarboxylate
20.0% of 3'-fluoro-4'-octyloxy-4-biphenylyl nonanoate
exhibits a broad smectic C* phase range and a high spontaneous polarization.

EXAMPLE 10

Step 1

Preparation 4-octyloxy-3'-fluoro-4'-biphenol

4-Octyloxy-4'-benzyloxy-3'-fluorobiphenyl (0.57 mol /obtained by cross-coupling of 3-fluoro-4-benzyloxyphenylboronic acid with 4-octyloxybromobenzene (as Example 1 STEP 2/3) is dissolved in ethylacetate and hydrogenated over Pd/C (1 g) until no further hydrogen is taken up. The mixture is then filtered, evaporated to dryness and crystallized.

Step 2

Preparation of 4'-octyloxy-3-fluoro-4-biphenylyl (trans-4-heptylcyclohexanecarboxylate)

The product from STEP 1 (0.005 mol) is added to a mixture of trans-4-propylcyclohexylcarboxyl chloride (0.005 mol), dry dichloromethane (20 ml) and triethylamine (1 ml). After treatment as Example 2 a white solid, C 40° S$_c$ 142.4° S$_A$ 146.4° N 173.9° I is obtained.

Analogously are obtained:
4'-octyloxy-3-fluoro-4-biphenylyl(trans-4-ethylcyclohexane carboxylate)
4'-octyloxy-3-fluoro-4-biphenylyl(trans-4-propylcyclohexane carboxylate)
4'-octyloxy-3-fluoro-4-biphenylyl(trans-4-butylcyclohexane carboxylate)
4'-octyloxy-3-fluoro-4-biphenylyl(trans-4-pentylcyclohexane carboxylate)
4'-octyloxy-3-fluoro-4-biphenylyl(trans-4-hexylcyclohexane carboxylate)
4'-octyloxy-3-fluoro-4-biphenylyl(trans-4-octylcyclohexane carboxylate)
4'-octyloxy-3-fluoro-4-biphenylyl(trans-4-nonylcyclohexane carboxylate)
4'-heptyloxy-3-fluoro-4-biphenylyl(trans-4-ethylcyclohexane carboxylate)
4'-heptyloxy-3-fluoro-4-biphenylyl(trans-4-propylcyclohexane carboxylate)
4'-heptyloxy-3-fluoro-4-biphenylyl(trans-4-butylcyclohexane carboxylate)
4'-heptyloxy-3-fluoro-4-biphenylyl(trans-4-pentylcyclohexane carboxylate)
4'-heptyloxy-3-fluoro-4-biphenylyl(trans-4-hexylcyclohexane carboxylate)
4'-heptyloxy-3-fluoro-4-biphenylyl(trans-4-heptylcyclohexane carboxylate)
4'-heptyloxy-3-fluoro-4-biphenylyl(trans-4-nonylcyclohexane carboxylate)

EXAMPLE 11

A liquid crystal mixture consisting of
20.0% of 4-heptyl-2-fluorophenyl(4'-octyloxy-3'-fluoro4-biphenylyl carboxylate)
20.0% of 4'-heptyl-2',3'-difluoro-4-biphenylyl(trans-4-heptylcyclohexane carboxylate)
20.0% of 4'-octyloxy-3-fluoro-4-biphenylyl(trans-4heptylcyclohexane carboxylate)
10% of 4-octyloxy-2,3-difluorophenyl(trans-4-heptylcyclohexane carboxylate)
15% of 4-pentyl-2-fluorophenyl(4-octyloxybenzoate)
8% of 4'-octyloxy-2',3'-difluoro-4-biphenylyl(4-methylhexanoate)

5.6% of optical active (1-cyano-2-methylpropyl)(4'-octyloxy-3'-fluoro-4-biphenylyl carboxylate) and 1.4% of optical active (1-cyanoethyl)(4'-octyloxy-3'-fluoro-4-biphenylyl carboxylate)

exhibits $S_c^*$ 59.4° $S_A$ 62.2° Ch 97.9° and a pulse response time (at 10 v/μm and at 30° C.) of 35 μs.

We claim:

1. A chiral, tilted, smectric liquid crystal phase comprising a mixture of at least two compounds, wherein at least one compound is an achiral fluorinated biphenyldiole of formula Ia

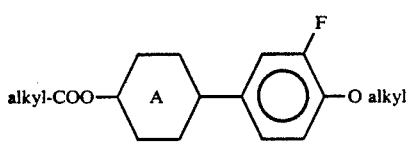
(Ia)

wherein alkyl each independently represents straight-chained alkyl with 5 to 12 carbon atoms, and

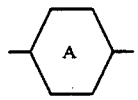

denotes a 1,4-phenylene group optionally substituted by 1-4 F atoms.

2. A phase according to claim 1 further comprising at least one compound selected from the formulae IV to VIII,

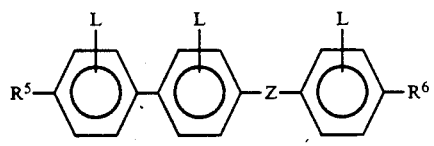
(IV)

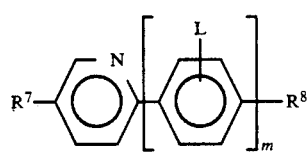
(V)

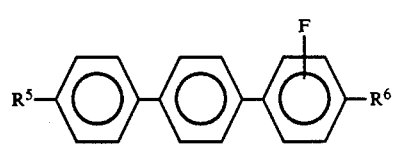
(VI)

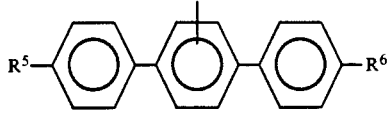
(VII)

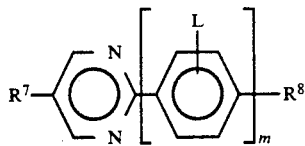
(VIII)

wherein $R^5$, $R^6$ and $R^8$ are each alkyl or alkoxy with 5 to 15 C atoms, Z is —CO—O— or a single bond, L is hydrogen or fluorine, $R^7$ is alkyl with 5 to 15 C atoms and m is 1 or 2.

3. A phase according to claim 1, further comprising at least one chiral dopant of the formula IX

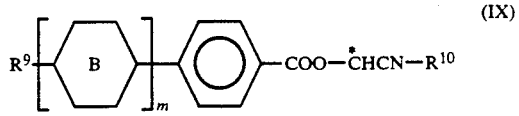
(IX)

wherein $R^9$ is alkyl or alkoxy with 5 to 15 C atoms, $R^{10}$ is alkyl with 1 to 8 C atoms, m is 1 or 2, and B is 1,4-phenylene, pyridine-2,5-diyl, pyrimidine-2,5-diyl or trans-1,4-cyclohexylene.

4. A phase according to claim 1, further comprising at least one chiral dopant of the formua IX

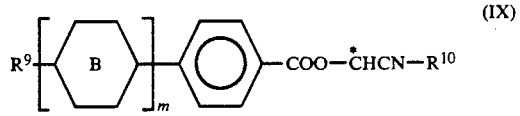
(IX)

wherein $R^9$ is alkyl or alkoxy with 5 to 15 C atoms, $R^{10}$ is alkyl with 1 to 8 C atoms, m is 1 or 2, and B is 1,4-phenylene, pyridine-2,5-diyl, pyrimidine-2,5-diyl or trans-1,4-cyclohexylene.

5. A phase according to claim 2, further comprising at least one chiral dopant of the formula IX

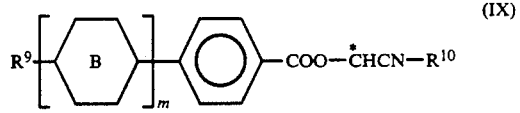
(IX)

wherein $R^9$ is alkyl or alkoxy with 5 to 15 C atoms, $R^{10}$ is alkyl with 1 to 8 c atoms, m is 1 or 2, and B is 1,4-phenylene, pyridine-2,5-diyl, pyridimide-2,5-diyl or trans-1,4-cyclohexylene.

* * * * *